United States Patent
Jojiki (10) Patent No.: US 7,322,697 B2
(45) Date of Patent: Jan. 29, 2008

(54) METHOD AND DEVICE FOR MEASURING PUPIL DISTANCE

(75) Inventor: Masao Jojiki, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 452 days.

(21) Appl. No.: 10/951,702

(22) Filed: Sep. 29, 2004

(65) Prior Publication Data

US 2005/0068495 A1    Mar. 31, 2005

(30) Foreign Application Priority Data

Sep. 30, 2003    (JP)    ............... 2003-341642

(51) Int. Cl.
*A61B 3/10*    (2006.01)

(52) U.S. Cl. ............ 351/204; 351/200; 351/206; 351/205

(58) Field of Classification Search ............ 351/204
See application file for complete search history.

(56) References Cited

U.S. PATENT DOCUMENTS

| | | | | |
|---|---|---|---|---|
| 4,190,331 A | * | 2/1980 | Padula et al. ............ | 351/204 |
| 5,033,840 A | * | 7/1991 | Hennequin et al. ...... | 351/204 |
| 5,822,032 A | * | 10/1998 | Edwards et al. ......... | 351/204 |
| 5,891,567 A | * | 4/1999 | Kim et al. ............... | 428/364 |

2003/0107806 A1    6/2003    Jojiki et al.

FOREIGN PATENT DOCUMENTS

| | | |
|---|---|---|
| JP | 6-205740 | 7/1994 |
| JP | 2003-195185 | 7/2003 |

OTHER PUBLICATIONS

Excerpt from "Optical Tools & Accessory" 2004 General Catalog of San Nishimura Co. Ltd., Product Nos. 455, 456, and 457 together with an English language translation of the same.
U.S. Appl. No. 09/611,364 to Abe et al., filed Jul. 6, 2000.

* cited by examiner

Primary Examiner—Jessica T Stultz
(74) Attorney, Agent, or Firm—Greenblum & Bernstein, P.L.C.

(57) ABSTRACT

There is provided a method of measuring a pupil distance, which includes locating an imaging device at a position a predetermined distance away from a member attached to eyeglasses worn by a subject. The member has two indicators. The method further includes photographing the subject while the subject observes an observing point in the vicinity of the imaging device, measuring an apparent distance E between left and right pupils on a photographed image, and obtaining an interpupillary distance PD in accordance with $PD=[(A+B) \times C \times E]/(A \times D)$ where "A" represents a distance between the member and the imaging device, "B" represents a distance between a center of rotation and the member, "C" represents an actual distance between the indicators, and "D" represents an apparent distance between the indicators.

15 Claims, 7 Drawing Sheets

METHOD AND DEVICE FOR MEASURING PUPIL DISTANCE

BACKGROUND OF THE INVENTION

The present invention relates to a method and a device for measuring a pupil distance including an interpupillary distance and a monocular pupil distance between a center line of a bridge of a nose of a subject and a pupil of each of left and right eyes of the subject.

Eyeglasses and binocular magnifying glasses are configured such that optical axes of left and right lenses (left and right optical systems) for left and right eyes are located at pupil positions of a wearer. To determine a distance between left and right optical axes of the left and right lenses (or left and right optical system), it is required to measure an interpupillary distance of the user. The interpupillary distance is a distance between centers of pupils of left and right eyes measured when a person observes a distant, forward object. The interpupillary distance is equal to a distance between centers of rotation of left and right eyes.

In general, a PD meter or a measurement device for measuring an interpupillary distance provided in a refractive power measurement device (which is used to measure power objectively) is used to measure the interpupillary distance. However, such conventional devices for measuring the interpupillary distance (e.g., the PD meter and the measuring device provided in the refractive power measurement device) have complicated structures and are expensive.

Japanese Patent Provisional Publication No. HEI 6-205740 discloses a measurement device for measuring an interpupillary distance. The measurement device disclosed in this publication includes two plates slidably attached to each other. Each plate has a measurement window in which a center line is formed perpendicularly to a sliding direction. One of the plates has scale marks and the other of the plates has a pointer.

A subject (a person to be tested) holds the measurement device and adjusts the measurement device so that the center lines in the measurement windows coincide with centers of pupils of the subject, respectively, while observing an object through the measurement windows. By reading the scale marks pointed by the pointer, the interpupillary distance of the subject is obtained.

One of problems of the measurement device disclosed in the above mentioned publication is that the subject is required to conduct the adjustment of the measurement device while holding the measurement device. In such a case, the measurement device tends to become unstable, by which the measurement of the interpuillary distance becomes difficult.

A digital PD meter of a product number NO.455 is available from SAN NISHIMURA CO.,LTD. However, this digital PD meter has disadvantages that measuring mistakes or a measuring error tend to occur because the digital PD meter is pressed against a face of a subject to conduct measurement.

PD meters of product numbers NO.456 and NO.457 are also available from SAN NISHIMURA CO.,LTD. However, the PD meter of this type also has disadvantages that the PD meter does not solve the disadvantages of the digital PD meter and the measurement result of the PD meter tends to be deteriorated by convergence.

SUMMARY OF THE INVENTION

The present invention is advantageous in that it provides a method and device for measuring a pupil distance easily, steadily and at a low cost.

According to an aspect of the present invention, there is provided a method of measuring a pupil distance. The method includes locating an imaging device at a position a predetermined distance away from a member attached to eyeglasses worn by a subject. The member has two indicators. The method further includes photographing the subject while the subject observes an observing point in the vicinity of the imaging device, measuring an apparent distance between left and right pupils of the subject on a photographed image, and obtaining an interpupillary distance PD in accordance with:

$$PD=[(A+B)\times C\times E]/(A\times D) \tag{1}$$

where "A" represents a distance between the member and the imaging device, "B" represents a distance between a center of rotation of each eye of the subject and the member, "C" represents an actual distance between the indicators in a direction parallel with a line connecting left and right centers of rotation of the subject, "D" represents an apparent distance between the indicators in the direction parallel with the line connecting the left and right centers of rotation on the photographed image, and "E" represents the apparent distance between the left and right pupils of the subject on the photographed image.

With this configuration, the interpupillary distance PD is obtained steadily, easily and at a low cost.

According to another aspect of the present invention, there is provided a method of measuring a pupil distance. The method includes locating an imaging device at a position a predetermined distance away from a member attached to eyeglasses worn by a subject. The member has two indicators. The method further includes photographing the subject while the subject observes an observing point in the vicinity of the imaging device, measuring apparent distances between a center line of a bridge of a nose of the subject and centers of left and right pupils of the subject on a photographed image, and obtaining a left monocular pupil distance PDL and a right monocular pupil distance PDR in accordance with:

$$PDL=[(A+B)\times C\times EL]/(A\times D) \tag{2}$$

$$PDR=[(A+B)\times C\times ER]/(A\times D) \tag{3}$$

where "A" represents a distance between the member and the imaging device, "B" represents a distance between a center of rotation of each eye of the subject and the member, "C" represents an actual distance between the indicators in a direction parallel with a line connecting left and right centers of rotation of the subject, "D" represents an apparent distance between the indicators in the direction parallel with the line connecting the left and right centers of rotation on the photographed image, "EL" represents an apparent distance between the center line of the bridge of the nose of the subject and the center of the left pupil of the subject on the photographed image, and "ER" represents an apparent distance between the center line of the bridge of the nose of the subject and the center of the right pupil of the subject on the photographed image.

With this configuration, the left monocular pupil distance PDL and the right monocular pupil distance PDR are obtained steadily, easily and at a low cost.

With regard to the above mentioned two aspects of the invention, the imaging device may be located at the position such that an optical axis of an imaging optical system of the imaging device is substantially included in a reference plane which is orthogonal to the line connecting the left and right centers of rotation of eyes of the subject and includes the center line of the bridge of the nose of the subject.

In a particular case, the member may be formed to be a plate member.

According to another aspect of the present invention, there is provided a method of measuring a pupil distance. The method includes locating an imaging device at a position a predetermined distance away from a member attached to eyeglasses worn by a subject. The member has two indicators. The method further includes photographing the subject while the subject observes an observing point in the vicinity of the imaging device, measuring apparent distances between a center line of a bridge of a nose of the subject and centers of left and right pupils of the subject on a photographed image, and obtaining an angle θ formed between an optical axis of an imaging optical system of the imaging device and a reference plane which is orthogonal to a line connecting left and right centers of rotation of eyes of the subject and includes the center line of the bridge of the nose of the subject.

The method further includes obtaining a left monocular pupil distance PDL and a right monocular pupil distance PDR in accordance with:

$$PDL=[(A+B)\times EL\times C/(D\times A)]+B\times \tan \theta \quad (4)$$

$$PDR=[(A+B)\times ER\times C/D+A\times B\times \tan \theta]/(A+2B) \quad (5)$$

where "A" represents a distance between the member and the imaging device, "B" represents a distance between the center of rotation of each eye of the subject and the member, "C" represents an actual distance between the indicators in a direction parallel with the line connecting the left and right centers of rotation of the subject, "D" represents an apparent distance between the indicators in the direction parallel with the line connecting the left and right centers of rotation on the photographed image, "EL" represents an apparent distance between the center line of the bridge of the nose of the subject and the center of the left pupil of the subject on the photographed image, and "ER" represents an apparent distance between the center line of the bridge of the nose of the subject and the center of the right pupil of the subject on the photographed image.

With this configuration, the left monocular pupil distance PDL and the right monocular pupil distance PDR are obtained steadily, easily and at a low cost.

Optionally, the eyeglasses may have a projection protruding toward a front side of the eyeglasses, and the angle θ is obtained based on an image of the projection on the photographed image.

In a particular case, the member may be formed to be a plate member.

According to another aspect of the present invention, there is provided a method of measuring a pupil distance. The method includes locating an imaging device at a position a predetermined distance away from a member attached to eyeglasses worn by a subject. The member has distance scale marks. The method further includes photographing the subject while the subject observes an observing point in the vicinity of the imaging device, measuring a distance between left and right pupils of the subject on a photographed image using the distance scale marks of the member on the photographed image, and obtaining an interpupillary distance PD in accordance with:

$$PD=[(A+B)\times F]/A \quad (6)$$

where "A" represents a distance between the member and the imaging device, "B" represents a distance between a center of rotation of each eye of the subject and the member, and "F" represents a distance between visual axes at a position of the member.

With this configuration, the interpupillary distance PD is obtained steadily, easily and at a low cost.

Optionally, the imaging device may be located at the position such that an optical axis of an imaging optical system of the imaging device is substantially included in a reference plane which is orthogonal to a line connecting left and right centers of rotation of eyes of the subject and includes a center line of a bridge of a nose of the subject.

According to another aspect of the present invention, there is provided a method of measuring a pupil distance. The method includes locating an imaging device at a position a predetermined distance away from a member attached to eyeglasses worn by a subject. The member has distance scale marks. The method further includes photographing the subject while the subject observes an observing point in the vicinity of the imaging device, measuring distances between a center line of a bridge of a nose of the subject and centers of left and right pupils of the subject on a photographed image using the distance scale marks of the member on the photographed image, and obtaining a left monocular pupil distance PDL and a right monocular pupil distance PDR in accordance with:

$$PDL=[(A+B)\times FL]/A \quad (7)$$

$$PDR=[(A+B)\times FR]/A \quad (8)$$

where "A" represents a distance between the member and the imaging device, "B" represents a distance between a center of rotation of each eye of the subject and the member, "FL" represents the distance between the center line of the bridge of the nose of the subject and the center of the left pupil of the subject measured on the photographed image using the distance scale marks of the member on the photographed image, and "FR" represents the distance between the center line of the bridge of the nose of the subject and the center of the right pupil of the subject measured on the photographed image using the distance scale marks of the member on the photographed image.

With this configuration, the left monocular pupil distance PDL and the right monocular pupil distance PDR are obtained steadily, easily and at a low cost.

Optionally, the imaging device may be located at the position such that an optical axis of an imaging optical system of the imaging device is substantially included in a reference plane which is orthogonal to a line connecting left and right centers of rotation of eyes of the subject and includes the center line of the bridge of the nose of the subject.

According to another aspect of the present invention, there is provided a method of measuring a pupil distance. The method includes locating an imaging device at a position a predetermined distance away from a member attached to eyeglasses worn by a subject. The member has distance scale marks. The method further includes photographing the subject while the subject observes an observing point in the vicinity of the imaging device, measuring distances between a center line of a bridge of a nose of the subject and centers of left and right pupils of the subject on a photographed image using the distance scale marks of the member on the photographed image, and obtaining an angle θ formed between an optical axis of an imaging optical system of the imaging device and a reference plane which is orthogonal to a line connecting left and right centers of rotation of eyes of the subject and includes the center line of the bridge of the nose of the subject.

The method further includes obtaining a left monocular pupil distance PDL and a right monocular pupil distance PDR in accordance with:

$$PDL=[(A+B)\times FL/A]+B\times \tan\theta \qquad (9)$$

$$PDR=[(A+B)\times FR+A\times B\times \tan\theta]/(A+2B) \qquad (10)$$

where "A" represents a distance between the member and the imaging device, "B" represents a distance between a center of rotation of each eye of the subject and the member, "FL" represents the distance between the center line of the bridge of the nose of the subject and the center of the left pupil of the subject measured on the photographed image using the distance scale marks of the member on the photographed image, and "FR" represents the distance between the center line of the bridge of the nose of the subject and the center of the right pupil of the subject measured on the photographed image using the distance scale marks of the member on the photographed image.

With this configuration, the left monocular pupil distance PDL and the right monocular pupil distance PDR are obtained steadily, easily and at a low cost.

Optionally, the eyeglasses may have a projection protruding toward a front side of the eyeglasses, and the angle θ is obtained based on an image of the projection on the photographed image.

According to another aspect of the present invention, there is provided a measuring device for measuring a pupil distance, which is provided with a frame to be worn on a face of a subject, a pair of aperture members having holes, respectively, and a pair of sliding mechanisms that slidably support the pair of aperture members in a predetermined direction, respectively, the pair of sliding mechanisms being fixed to the frame. The pair of sliding mechanisms are located on the frame such that the pair of aperture members can be moved to positions corresponding to left and right eyes of the subject, respectively.

With this configuration, the interpupillary distance PD is obtained steadily, easily and at a low cost.

Optionally, the predetermined direction may be substantially parallel with a line connecting the left and right eyes of the subject in a situation where the frame is worn on the surface of the subject.

Still optionally, the frame may be configured to be an eyeglass frame.

Still optionally, the measuring device may include a pair of lenses attached to the eyeglass frame. In this structure, the pair of lenses respectively have openings, and the pair of the sliding mechanisms are located at positions of the openings of the pair of lenses, respectively, and are fixed to the pair of lenses, respectively.

Still optionally, each of the sliding mechanism may include a sliding member that supports corresponding one of the pair of aperture members and has a screw hole, a guide rail on which the sliding member slides, and a pair of bases that support the guide rail at a nose side and an ear side of the guide rail, respectively. The pair of bases is fixed with respect to the frame. Further, each of the sliding mechanisms includes a screw that is rotatably supported by one of the bases located on the ear side and engages with the screw hole of the sliding member so that the sliding member slides on the guide rail by rotation of the screw.

In a particular case, one of the pair of sliding mechanisms may be configured such that the screw of the one of the pair of sliding mechanisms is used as a right-hand screw, and the other of the pair of sliding mechanisms is configured such that the screw of the other of the pair of sliding mechanisms is used as a left-hand screw.

In a particular case, each of the pair of aperture members may be configured to have a form of a circular disc. The hole of each of the pair of aperture members is located at a center of the form of the circular disc.

DETAILED DESCRIPTION OF THE EMBODIMENTS

Hereinafter, embodiments according to the invention are described with reference to the accompanying drawings.

First Embodiment

Figure 1:
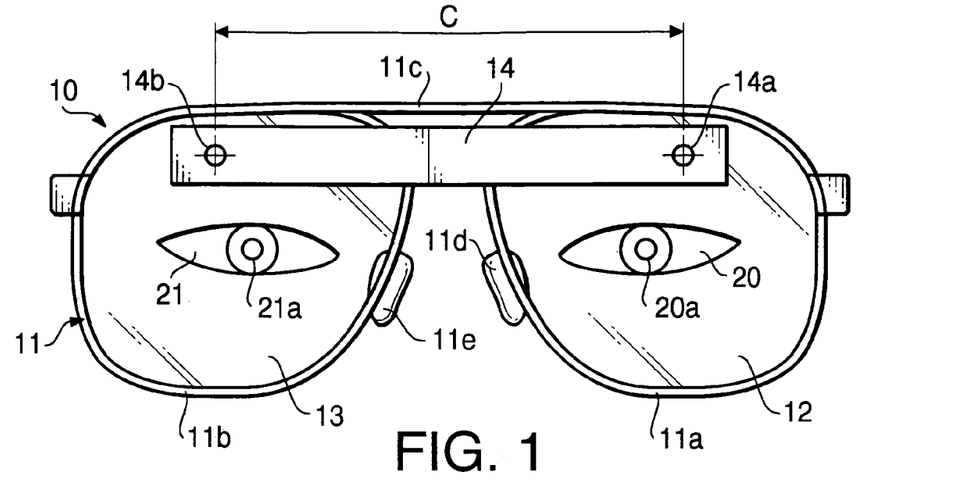
FIG. 1 is a front view of eyeglasses with a scale used in a method of measuring a pupil distance according to a first embodiment.
Figure 2:
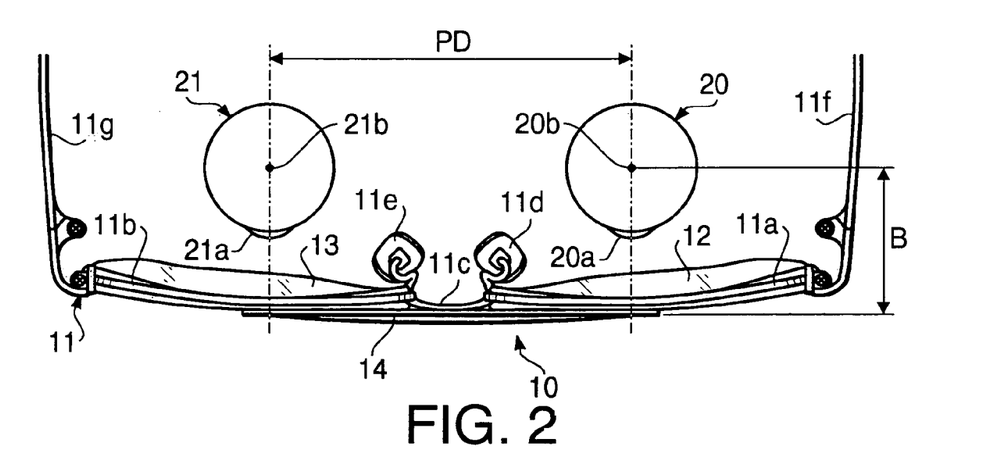
FIG. 2 is a plan view of the eyeglasses.
Figure 3:
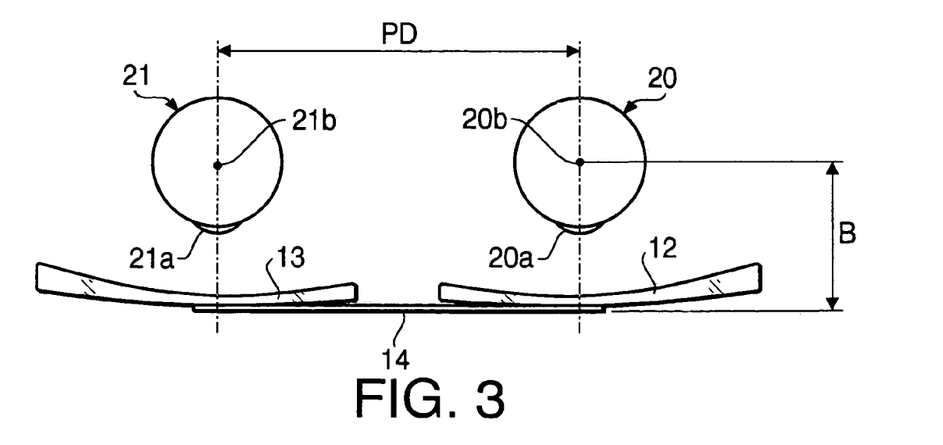
FIG. 3 is a plan view of the eyeglasses showing only eyes, the scale and lenses.

A method of measuring a pupil distance according to a first embodiment of the invention will be described. FIG. 1 is a front view of eyeglasses 10 with a scale used in the method of measuring the pupil distance according to the first embodiment. FIG. 2 is a plan view of the eyeglasses 10. The eyeglasses 10 have a frame 11, left and right lenses 12 and 13, and a scale 14 formed as a rectangular, plate member. The scale 14 is adhered to the left and right lenses 12 and 13 at the upper side of the lenses 12 and 13. As shown in FIG. 1, indicators 14a and 14b, each of which has a shape of a cross, are formed on the scale 14 at a distance C. FIG. 3 is a plan view of the eyeglasses 10 showing only eyes 20 and 21, the scale 14 and the lenses 12 and 13.

The frame 11 has rims 11a and 11b respectively supporting the lenses 12 and 13, a bridge 11c connected to the rims 11a and 11b, nose pads 11d and 11e, and temples 11f and 11g to be hooked to left and right ears.

It should be noted that the eyeglasses 10 can be easily configured by temporarily sticking the scale 14 on eyeglasses owned by a subject.

Alternatively, a plurality of types of eyeglasses 10 having lenses 12 and 13 having different dioptric powers may be prepared. In this case, one of the plurality of types of eyeglasses 10 is selected depending on visual acuity of the subject to measure an interpuilliary distance PD of the subject. Preferably, the plurality of types of eyeglasses includes eyeglasses having dioptric power of zero. If the subject does not usually wear eyeglasses, the eyeglasses having dioptric power of zero is selected to measure the interpuilliary distance of the subject.

The left and right eyes 20 and 21 are shown in FIGS. 1, 2 and 3. The eyes 20 and 21 have pupils 20a and 21a, respectively. When the subject moves his/her visual axes, the eyes 20 and 21 rotate about respective centers of rotation 20b and 21b. The interpulillary distance PD is a distance between the pupils 20a and 21a when the subject observes a distant, forward object and is equal to a distance between the centers of rotation 20b and 21b.

Figure 4:
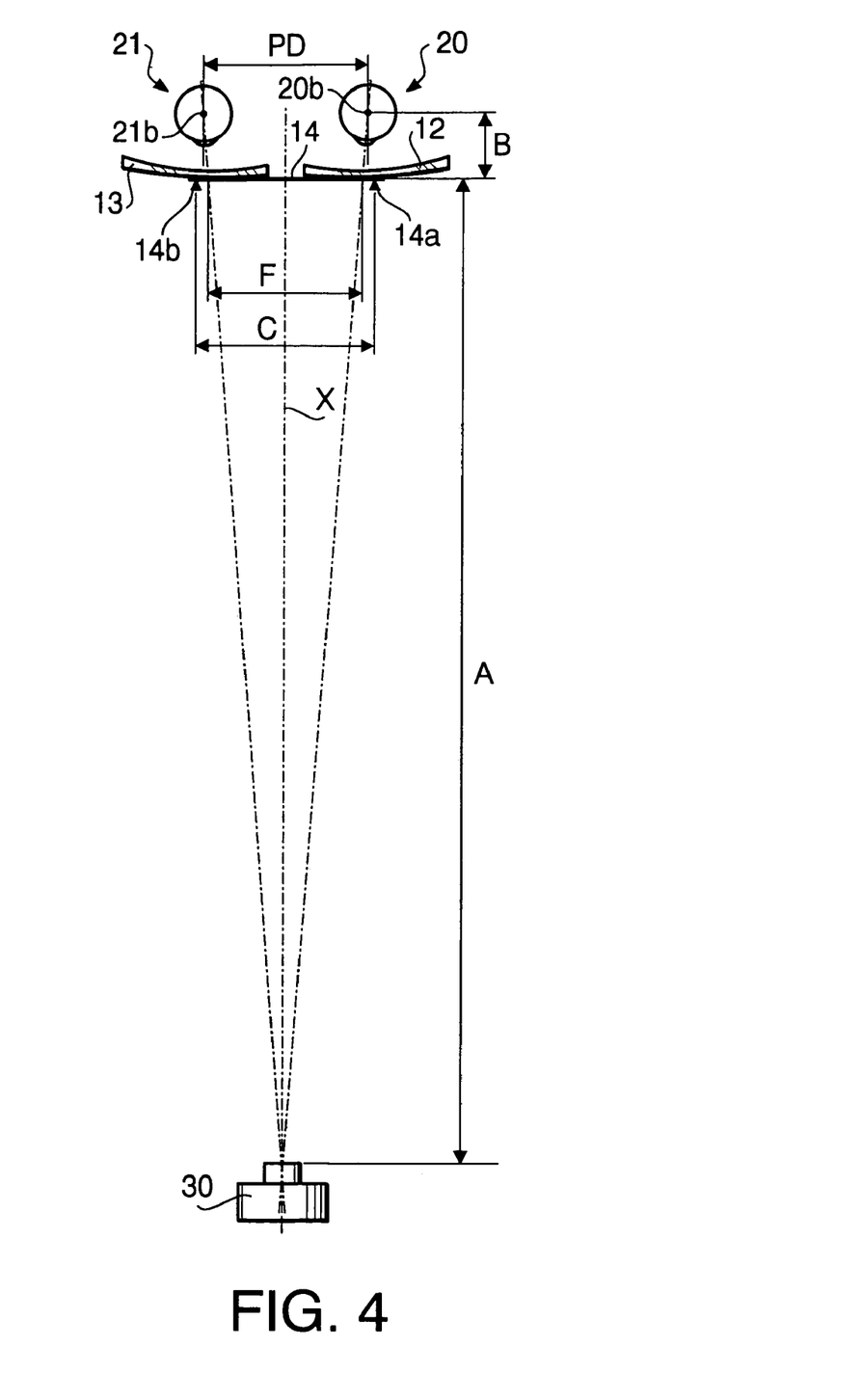
FIG. 4 shows a situation where a subject observes a camera to measure an interpupilary distance.

FIG. 4 shows a situation where the subject observes a near object (i.e., a camera 30) to measure the interpupilary distance PD. As shown in FIG. 4, when the subject observes the near object, the eyes 20 and 21 rotate inwardly and thereby the distance between the pupils 20a and 21a decreases in comparison with the interpupillary distance PD.

Since the distance between the centers of rotation 20b and 21b does not change while the eyes 20 and 21 rotates, the interpupillary distance PD is determined independently of an object distance. In FIG. 4, a distance from the center of rotation 20b (21b) to a front surface of the scale 14 is defined as a distance B, and a distance between the indicators 14a and 14b in a direction parallel with a line connecting the centers of rotation 20b and 21b is defined as the distance C.

Hereafter, a process for measuring the interpupillary distance PD using the eyeglasses 10 will be described. Firstly, the subject wears the eyeglasses 10. Then, as shown in FIG. 4, the camera 30 is placed at a distance A from the scale 14. More specifically, the camera 30 is located such that an optical axis X of a camera lens (i.e., an imaging optical system) of the camera 30 is included in a reference plane which includes a bridge of a nose of the subject and is perpendicular to the line connecting the centers of rotation 20b and 21b of the subject. In this situation, a face of the subject facing the front side is photographed while the subject observes the camera lens of the camera 30. In FIG. 4, the reference plane overlaps with the optical axis X.

Triangular marks in FIG. 4 indicate positions of the indicators 14a and 14b on the scale 14. The distance C represents the distance between the indicators 14a and 14b. Since the center of each pupil (20a, 21a) is located on the visual axis of each eye (20, 21), the interpupillary distance PD can be determined based on a distance between the visual axes of left and right eyes 20 and 21.

The distance between the visual axes changes depending on a position between the near object (the camera 30) and the eyes (20,21) because in such a situation the eyes 20 and 21 rotate inwardly and the visual axes intersect with each other at a point of fixation (i.e., the position of the camera 30). In this embodiment, the distance between the visual axes is obtained at the position of the scale 14. In FIG. 4, the distance between the visual axes at the position of the scale 14 is defined as a distance F.

Figure 5:
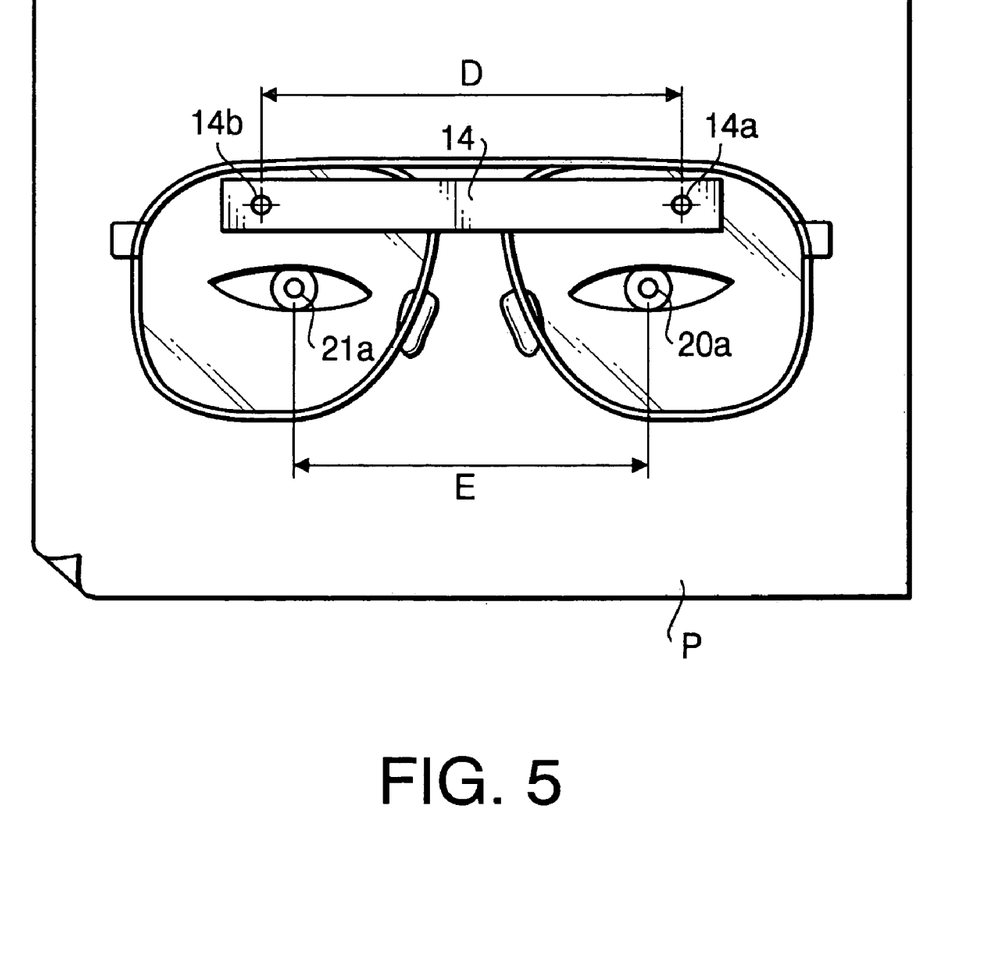
FIG. 5 shows an example of a photographed image of the eyeglasses worn by the subject in the situation shown in FIG. 4.

Next, the photographed image is printed, for example, on an A4-size sheet P. FIG. 5 shows an example of the photographed image. In FIG. 5, only a portion including the eyes and the eyeglasses 10 of the printed image is indicated for the sake of simplicity. Actually, the printed image includes a face of the subject.

By using the printed image (the sheet P) shown in FIG. 5, an apparent distance D between the indicators 14a and 14b on the sheet P in a direction parallel with the line connecting the left and right centers of rotation (20b, 21b) is measured. Also, an apparent distance E between the pupils 20a and 21a at the position of the scale 14 is measured by using the sheet P. It is noted the distance F is an actual distance between the pupils 20a and 21a and the distance E is an apparent distance between the pupils 20a and 21a on the sheet P.

Since a ratio between the apparent distance D and the distance C represents magnification of the image with regard to the scale 14, the actual distance F between the pupils 20a and 21a can be obtained by multiplying the apparent distance E by C/D. That is, the distance F is expressed by F=E×C/D.

It is understood from FIG. 4 that the interpupillary distance PD is expressed by PD=F×(A+B)/A because the interpupillary distance PD is equal to the distance between the centers of rotation 20b and 21b. By combining the above mentioned two equations, the interpupillary distance PD is expressed by the following equation (1).

$$PD=[(A+B) \times C \times E]/(A \times D) \quad (1)$$

A numerical example will be explained. Since a distance between a rear surface of the lens (12 or 13) and the center of rotation (20b or 21b) can be regarded as 25 mm, the distance B between the center of rotation 20b (21b) and the scale 14 is 28 mm assuming that the thickness of the lens 12 (13) and the scale 14 is 3 mm. Assuming that the distance A from the scale 14 to the camera 30 is 1 m, the distance C between the indicators 14a and 14b is 80 mm, and the measurement results of the distances D and E are 60 mm and 50 mm, respectively, the interpulillary distance PD [mm] is determined as follows.

$$PD=[(1000+28) \times 80 \times 50]/(1000 \times 60) \approx 68.5 \text{ mm}$$

In general, positions of left and right eyes are not precisely symmetrical with respect to a bridge of a nose of a person. Therefore, it is preferable that monocular pupil distances PDL and PDR for the left and right eyes (see FIG. 6) as well as the interpupillary distance PD are obtained to design binocular magnifying glasses for surgery. By using the left and right monocular pupil distances PDL and PDR, positions of left and right magnifying optical systems of the binocular magnifying glasses are determined.

The actual monocular pupil distances PDL and PDR are also obtained based on the sheet P (the printed image shown in FIG. 5). To obtain the distances PDL and PDR, an apparent distance EL between the center line of the bridge of the nose of the subject and the center of the pupil 20a of the left eye 20 is measured on the sheet P, and an apparent distance ER between the center line of the bridge of the nose of the subject and the center of the pupil 21a of the right eye 21 is also measured on the sheet P.

Next, the monocular pupil distances PDL and PDR are determined according to the following equations (2) and (3).

$$PDL=[(A+B) \times C \times EL]/(A \times D) \quad (2)$$

$$PDR=[(A+B) \times C \times ER]/(A \times D) \quad (3)$$

It is noted that each of the above mentioned equations (2) and (3) holds when the optical axis X of the camera 30 is included in the reference plane which includes the center line of the bridge of the nose of the subject and is perpendicular to the line connecting the centers of rotation 20b and 21b of the subject. Therefore, when the optical axis X is inclined with respect to the reference plane, each of the distance PDL and PDR obtained from the equations (2) and (3) includes an error. Meanwhile, the interpupillary distance PD obtained from the equation (1) does not include an error when the optical axis X is inclined with respect to the reference plane.

Figure 6:
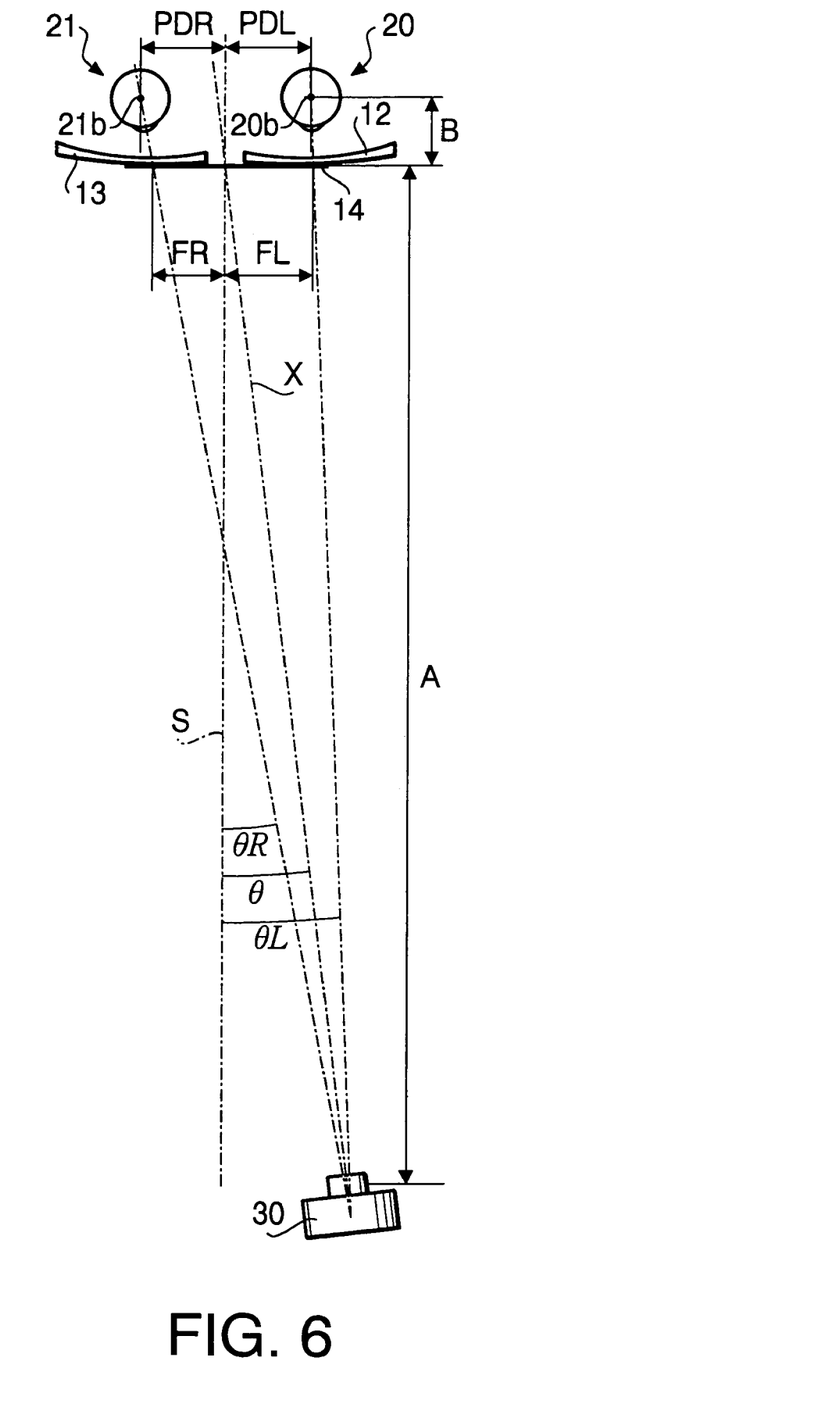
FIG. 6 shows a situation in which an optical axis of the camera is inclined with respect to a reference plane.

FIG. 6 shows a situation in which the optical axis X is inclined by an angle θ with respect to the reference plane S. In FIG. 6, an angle formed between the reference plane S and a line connecting the center of rotation 20b of the left eye 20 and the camera lens of the camera 30 is represented by an angle $θ_L$, and an angle formed between the reference plane S and a line connecting the center of rotation 21b of the right eye 21 and the camera lens of the camera 30 is represented by an angle $θ_R$.

The monocular pupil distance PDL is equal to a distance from the center line of the bridge of the nose of the subject to the center of rotation 20b, and the monocular pupil distance PDR is equal to a distance from the center line of the bridge of the nose of the subject to the center of rotation 21b. When a distance between the center line of the bridge of the nose of the subject and the center of the left pupil 20a is defined as a distance FL, and a distance between the center line of the bridge of the nose of the subject and the center of the right pupil 21a is defined as a distance FR, the following equations hold.

$$FL=PDL+B\times\tan θ_L$$

$$FR=PDR-B\times\tan θ_R$$

Further, the $\tan θ_L$ and $\tan θ_R$ can be expressed by the following equations.

$$\tan θ_L=(A \tan θ-PDL)/(A+B)$$

$$\tan θ_R=(A \tan θ+PDR)/(A+B)$$

Therefore, the following equations hold.

$$FL=PDL+B\times(A \tan θ-PDL)/(A+B)$$

$$FR=PDR-B\times(A \tan θ+PDR)/(A+B)$$

From the above equations, the following equations (9) and (10) are derived.

$$PDL=[(A+B)\times FL/A]+B\times\tan θ \quad (9)$$

$$PDR=[(A+B)\times FR+A\times B\times\tan θ]/(A+2B) \quad (10)$$

The distances FL and FR can be obtained from the sheet P (i.e., the printed image). More specifically, the distance FL is obtained from an apparent distance EL between the left pupil 20a and the center line of the bridge of the nose of the subject on the sheet P, and the distance FR is obtained from an apparent distance ER between the right pupil 21a and the center line of the bridge of the nose of the subject on the sheet P. The distance FL is expressed by FL=EL×C/D. The distance FR is expressed by FR=ER×C/D. By assigning these equations to the equations (9) and (10), the following equations (4) and (5) are obtained.

$$PDL=[(A+B)\times EL\times C/(D\times A)]+B\times\tan θ \quad (4)$$

$$PDR=[(A+B)\times ER\times C/D+A\times B\times\tan θ]/(A+2B) \quad (5)$$

Accordingly, the monocular pupil distances PDL and PDR can be obtained based on the apparent distances EL and ER on the printed image and the angle θ even if the optical axis X is not included in the reference plane S.

Figure 7:
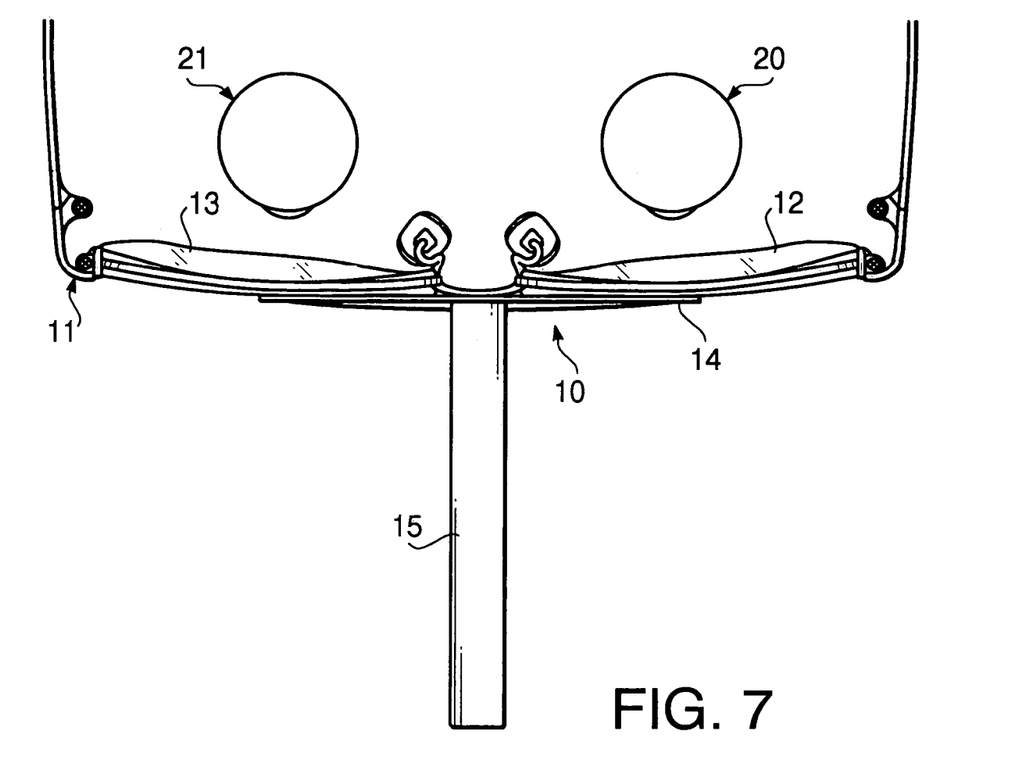
FIG. 7 is a plan view of the eyeglasses showing a situation where a projection is additionally attached to the eyeglasses to obtain the angle from the photographed image.

FIG. 7 is a plan view of the eyeglasses 10 showing a situation where a projection 15 is additionally attached to the eyeglasses 10 to obtain the angle θ from the printed image. As shown in FIG. 7, the projection 15 is formed to be a cylindrical rod, and is made of firm, lightweight material such as polystyrene foam. Although the projection 15 has a form of the cylindrical rod in this embodiment, the projection 15 may have another shape, for example, a rod-shaped rectangular solid.

The projection 15 protrudes toward the front side of the eyeglasses 10. By photographing the subject wearing the eyeglasses 10 having the projection 15, the angle θ of the optical axis X with respect to the reference plane is obtained from an image of the projection 15 on the photographed image.

Figure 12:
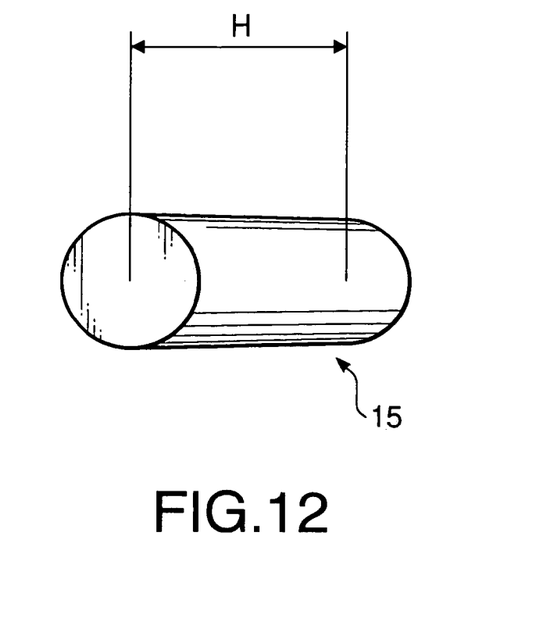
FIG. 12 shows an image of the projection on the photographed image when the optical axis of the camera is inclined with respect to the reference plane.

The angle θ is obtained as follows. When the projection 15 has the cylindrical shape (i.e., when the top surface of the projection 15 has a circular shape), if the angle θ is 0°, the projection 15 is imaged as a circle on the photographed image. By contrast, when the angle θ is not 0°, the projection 15 is imaged to have a circular portion corresponding to the top surface of the projection 15 and an oval portion corresponding to a side surface of the projection 15 as shown in FIG. 12. In FIG. 12, a distance between a center of the circle and a center of a circular arc portion of the oval portion is defined as a distance H.

Figure 13:
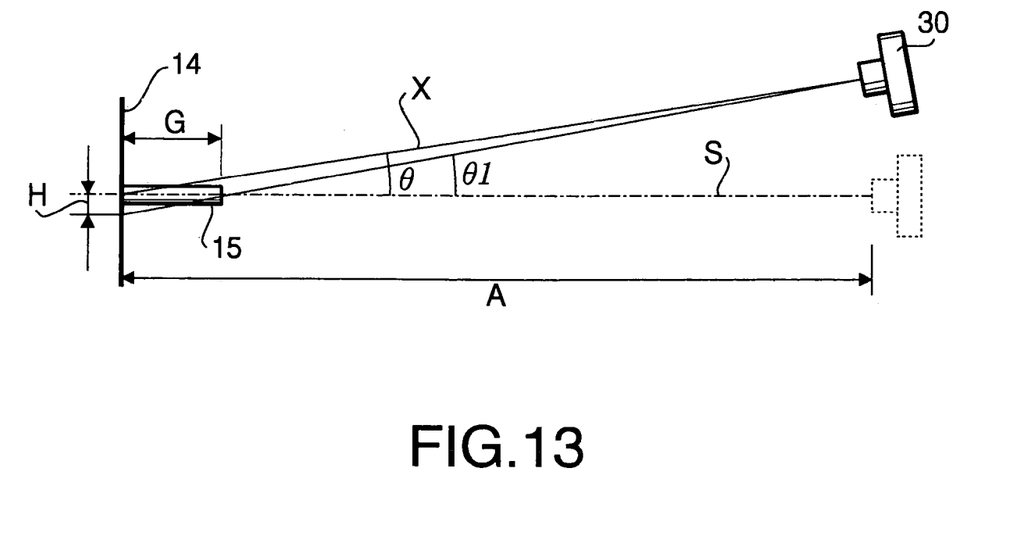
FIG. 13 shows a situation where the projection attached to the eyeglasses is photographed when the optical axis of the camera is inclined with respect to the reference plane.

By obtaining the distance H, the angle θ is obtained. As shown in FIG. 13, an angle formed by a line corresponding to a line of sight from the camera 30 to the top end of the projection 15 with respect to the reference plane is defined as an angle θ1. Assuming that a distance between the camera 30 to the scale 14 is a distance A and the length of the projection 15 is a length G, the distance H is expressed by the following equation.

$$H=A \tan(θ-θ1)$$

Since $A \tan θ=(A-G)\tan θ1$ holds, the angle θ is determined according to the following equation.

$$θ=[(A-G)/G]\times\tan^{-1}(H/A)$$

According to this equation, if the distance A is 1000 mm, the length G is 100 mm, and the distance H is 5.8 mm, the angle θ is 3°.

As described above, according to the first embodiment, the pupil distance is obtained steadily, easily and at a low cost because only the scale and the camera 30 is required to measure the pupil distance. The pupil distance can be determined with high precision. A burden on the subject during the measurement process can be decreased.

Second Embodiment

Figure 8:
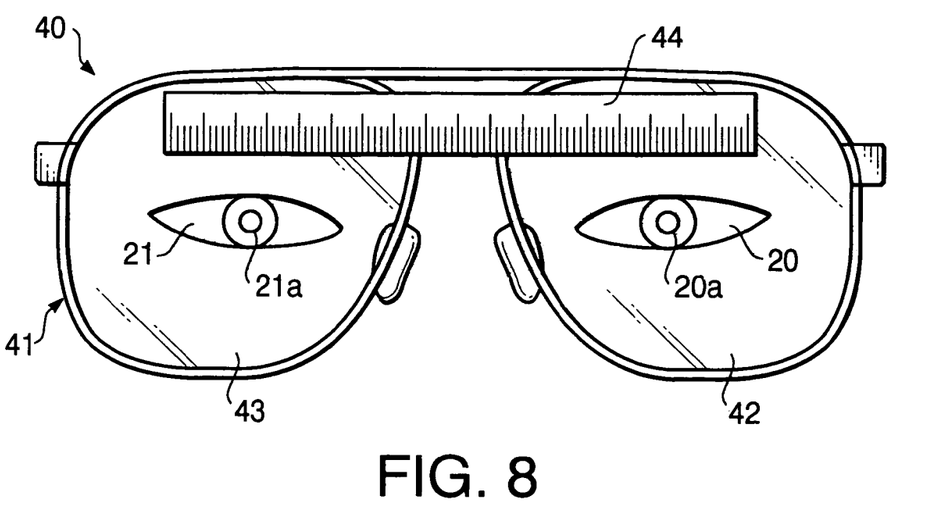
FIG. 8 is a front view of eyeglasses with a scale used in a method of measuring a pupil distance according to a second embodiment.

A method of measuring a pupil distance according to a second embodiment of the invention will be described. FIG. 8 is a front view of eyeglasses 40 with a scale used in the method of measuring the pupil distance according to the second embodiment.

The eyeglasses 40 have a frame 41, left and right lenses 42 and 43, and a scale 44 labeled with distance scale marks. The scale 44 is adhered to the left and right lenses 42 and 43 at the upper side of the lenses 42 and 43. In FIG. 8, to elements which are the same as those of the first embodiment, the same reference numbers are assigned, and the explanations thereof will not be repeated. Since the frame 41 has the same structure as that of the frame 11 of the first embodiment, the explanation of the frame 41 is not repeated. A plan view of the eyeglasses 40 is substantially the same as FIG. 2.

Various distances (A,B,F,FL and FR) defined in FIGS. 2 through 6 in the first embodiment are also used to describe the method according to the second embodiment.

Hereafter, a process for measuring the interpupillary distance PD will be described. Firstly, the subject wears the eyeglasses 40. Then, similarly to the first embodiment, the camera 30 is placed at the distance A from the scale 44 as shown in FIG. 4. More specifically, the camera 30 is located such that the optical axis X of the camera lens of the camera 30 is included in the reference plane which includes the bridge of the nose of the subject and is perpendicular to the line connecting the centers of rotation 20$b$ and 21$b$ of the subject. In this situation, a face of the subject facing the front side is photographed while the subject observes the camera lens of the camera 30.

Next, the photographed image is printed, for example, on an A4-size sheet. The distance F between the left and right pupils 20$a$ and 21$a$ is then measured on the printed image by using the scale 44 having the distance scale marks. It is noted that the actual distance F between the pupils 20$a$ and 21$a$ can be obtained by utilizing an image of the scale 44 on the printed image because the scale 44 is scaled up or scaled down according to shooting magnification. That is, the actual distance between the pupils at the position of the scale 44 is obtained by using the scale 44 having the distance scale marks.

After the distance F is obtained, the interpupillary distance PD is obtained according to the following equation (6).

$$PD=[(A+B)\times F]/A \quad (6)$$

In this equation (6), "A" represents the distance A between the camera 30 and the scale 44, and "B" represents the distance B between the center of rotation of the eye and the front surface of the scale 44. In an example of FIG. 8, the distance F is 65 mm, and therefore the interpupillary distance PD is determined to be 66.8 mm from the equation (6).

To obtained the monocular pupil distances PDL and PDR, the distances FL and FR are measured from the image of the scale 44 on the printed image. That is, the distance FL between the center line of the bridge of the nose of the subject and the left pupil 20$a$ is measured using the image of the scale 44 on the printed image, and the distance FR between the center line of the bridge of the nose of the subject and the right pupil 21$a$ is also measured using the image of the scale 44 on the printed image.

Then the distances PDL and PDR are obtained according to the following equations (7) and (8).

$$PDL=[(A+B)\times FL]/A \quad (7)$$

$$PDR=[(A+B)\times FR]/A \quad (8)$$

By reading the scale marks of the scale 44 shown in the example of FIG. 8, the distances FL and FR are determined as 31 mm and 34 mm, respectively. Therefore, in this case the PDL and PFR are determined to be 31.9 mm and 34.9 mm, respectively, from the above mentioned equations (7) and (8).

It is noted that each of the above mentioned equations (7) and (8) holds when the optical axis X of the camera 30 is included in the reference plane. Therefore, when the optical axis X is inclined with respect to the reference plane, each of the distance PDL and PDR obtained from the equations (7) and (8) includes an error.

When the optical axis X is inclined with respect to the reference plane, the distances PDL and PDR can be obtained from the above mentioned equations (9) and (10) as explained in detail in the first embodiment.

$$PDL=[(A+B)\times FL/A]+B\times\tan\theta \quad (9)$$

$$PDR=[(A+B)\times FR+A\times B\times\tan\theta]/(A+2B) \quad (10)$$

As described above, according to the second embodiment, the pupil distance is obtained steadily, easily and at a low cost because only the scale 44 and the camera 30 is required to measure the pupil distance. The pupil distance can be determined with high precision. A burden on the subject during the measurement process can be decreased.

Third Embodiment

Figure 9:
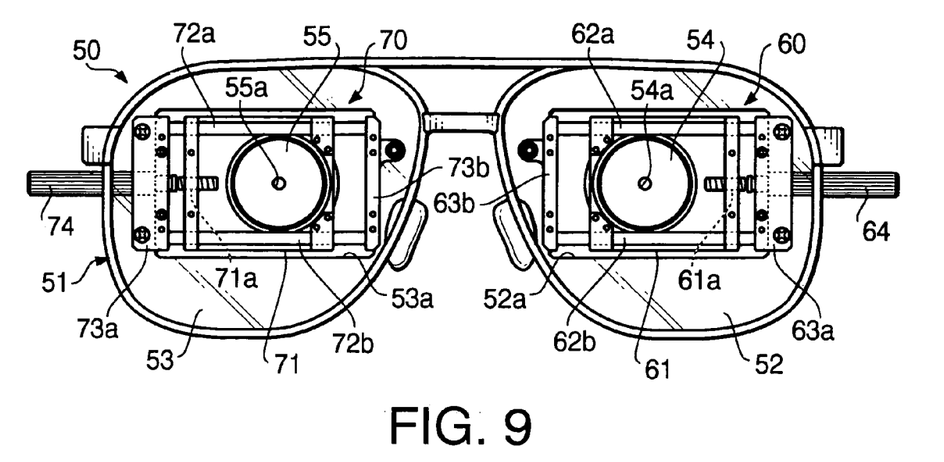
FIG. 9 is a front view of a measuring device according to a third embodiment.
Figure 10:
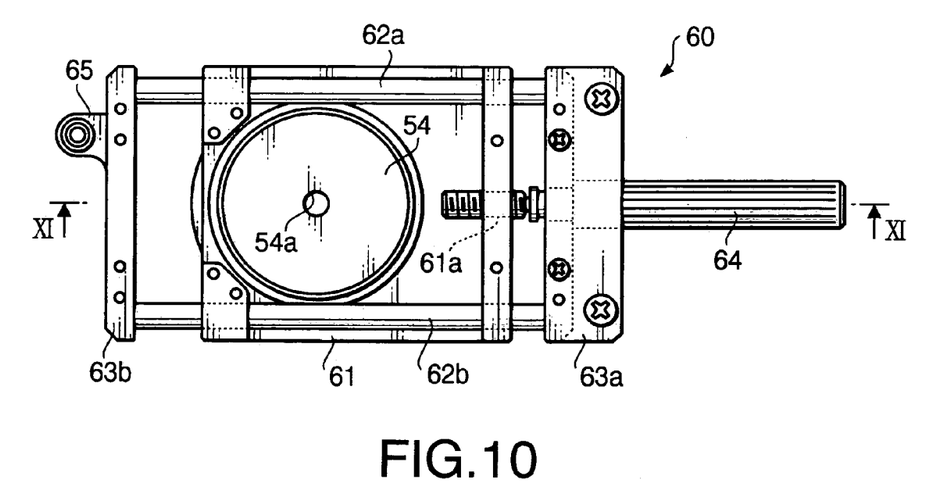
FIG. 10 is an enlarged view illustrating a sliding mechanism of the measuring device.
Figure 11:
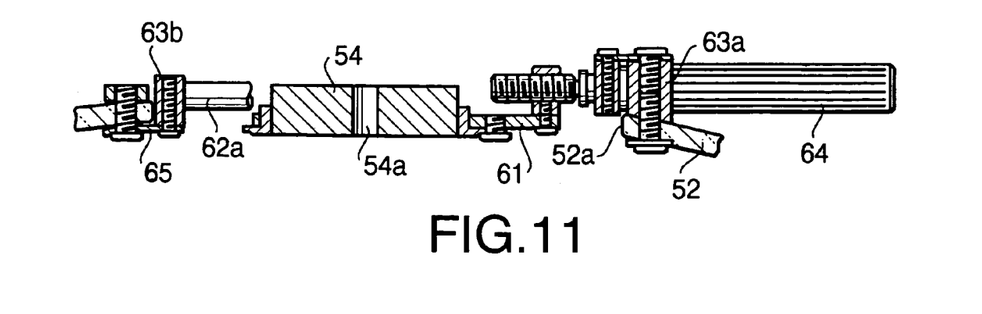
FIG. 11 is a cross sectional view of the sliding mechanism taken along a line XI-XI in FIG. 10.

A device for measuring a pupil distance according to a third embodiment will be described. FIG. 9 is a front view of a measuring device 50 according to the third embodiment. The measuring device 50 is used to measure the pupil distance. FIG. 10 is an enlarged view illustrating a sliding mechanism 60 of the measuring device 50. FIG. 11 is a cross sectional view of the sliding mechanism 60 taken along a line XI-XI in FIG. 10.

As shown in FIG. 9, the measuring device 50 includes a frame 51, left and right lenses 52 and 53 attached to the frame 51, a pair of aperture members 54 and 55 each of which has a form of a circular disc, and a pair of sliding mechanisms 60 and 70. The aperture member 54 is located at a position of an opening 52$a$ formed on the lens 52 and has a circular hole 54$a$ at the center thereof. The aperture member 55 is located at a position of an opening 53$a$ formed on the lens 53 and has a circular hole 55$a$ at the center thereof.

The sliding mechanism 60 supports the aperture member 54 so that the aperture member 54 is slidable in the horizontal direction (a right and left direction in FIG. 9). The sliding mechanism 70 supports the aperture member 55 so that the aperture member 55 is slidable in the horizontal direction (a right and left direction in FIG. 9). The diameter of each of the holes 54$a$ and 55$a$ is 3 mm in this embodiment.

As shown in FIGS. 10 and 11, the sliding mechanism 60 includes a sliding member 61, a pair of guide rails 62$a$ and 62$b$ for guiding the sliding member 61, and first and second bases 63$a$ and 63$b$ which support the guide rails 62$a$ and 62$b$ at the left and right end portions of the guide rails 62$a$ and 62$b$. Further, the sliding mechanism 60 includes a screw 64 for moving the sliding member 61 in the left and right direction by rotating motion of the screw 64. The screw 64 is rotatably attached to the first base 63$a$ and engages with a screw hole 61$a$ formed on the sliding member 61.

The first base 63$a$ is fixed to the lens 52 by two bolts at an ear side of the opening 52$a$. The second base 63$b$ is fixed to the lens 52 through a bracket 65 by a bolt at a nose side of the opening 52$a$.

Similarly to the sliding mechanism 60, the sliding mechanism 70 includes a sliding member 71, guide rails 72$a$ and 72$b$, first and second bases 73$a$ and 73$b$, and a screw 74 for moving the sliding member 71 in the left and right direction by rotating motion of the screw 74. The screw 74 is rotatably attached to the first base 73$a$ and engages with a screw hole 71$a$ formed on the sliding member 71. Since the sliding mechanism 70 has the same structure as that of the sliding member 60, detailed explanation thereof is not repeated.

The screw hole 61a and the screw 64 are configured such that the screw 64 is used as a left-hand screw. Therefore, the sliding member 61 slides toward the nose side by rotating the screw 64 clockwise when the screw 64 is viewed from the left ear side. The screw hole 71a and the screw 74 are configured such that the screw 74 is used as a right-hand screw. Therefore, the sliding member 71 slides toward the nose side by rotating the screw 74 counterclockwise when the screw 74 is viewed from the right ear side.

A measuring process using the measuring device 50 is as follows. Firstly, the subject wears the measuring device 50 in a manner that the subject wears his/her eyeglasses. Then, the subject adjusts the screws 64 and 74 so that left and right fields of view of the left and right eyes observed through the holes 54a and 55a of the aperture members 54 and 55 coincide with each other while observing an observing point, which is, for example, more than 5 meter away from the subject, through the holes 54a and 55a.

As described above, the screws 64 and 74 have an inverse relationship (i.e., the screw 64 is a left-hand screw and the screw 74 is a right-hand screw). Therefore, both of the aperture members 54 and 55 move toward the nose side while the subject rotates the screws 64 and 74 clockwise when the screws 64 and 74 are viewed from the left ear side. On the other hand, both of the aperture members 54 and 55 move toward the respective ear sides while the subject rotates the screws 64 and 74 counterclockwise when the screws 64 and 74 are viewed from the left ear side.

In general, a person who wears the eyeglasses 50 acts to move both of the left and right aperture members 54 and 55 toward the respective ear sides when the pupils are at the outside of the respective holes (54a and 55a), and acts to move both of the left and right aperture members 54 and 55 toward the nose side when the pupils are at the inside of the respective holes (54a or 55a). The aperture members 54 and 55 move toward the nose side when the screws 64 and 74 are rotated in the same direction when the screws 64 and 74 are viewed from one of the left and right ear sides. Also, the aperture members 54 and 55 move toward the respective ear sides when the screws 64 and 74 are rotated in the same direction when the screws 64 and 74 are viewed from one of the left and right ear sides.

With this structure, the subject can easily adjust the left field view to the right field of view using the screws 64 and 74. Therefore, according to the measuring device 50, usability is increased.

After the left and right fields of view coincide with each other, the measuring device 50 is detached from the subject. Then, a distance between the centers of the left and right holes 54a and 55a is measured by using, for example, a micrometer or calipers. The measured distance is the interpupillary distance PD.

As a variation of the third embodiment, the measuring device 50 may be configured to additionally have a scale like the scale 44 shown in FIG. 8 on the upper side of the sliding mechanisms 60 and 70, and to have pointers capable of pointing positions of the holes 54a and 55a on the scale. After the left and right fields of view are adjusted using the screws 64 and 74, the distance between the centers of the holes 54a and 55a are read from the scale. The read data is the interpupillary distance PD.

As described above, according to the third embodiment, the pupil distance is obtained steadily, easily and at a low cost.

In the following, the advantages of the first thorough third embodiments of the invention are explained. One of the above mentioned methods and device for measuring the pupil distance according to the embodiments may be used to produce binocular magnifying glasses for surgery. Such a binocular magnifying glasses is disclosed, for example, in Japanese Patent Provisional Publication No. 2003-195185.

A diameter of an exit pupil of each magnifying optical system of the binocular magnifying glasses is approximately 4 mm, and a diameter of the pupil under an illumination lamp for surgery is approximately 3 mm. Therefore, the centers of the exit pupils of the magnifying optical system and centers of pupils of a wearer (a person wears the binocular magnifying glasses) are required to be coincide with each other within an accuracy better than or equal to ±0.5 mm. That is, to manufacture the binocular magnifying glasses, it is required to obtain an accurate pupil distance (e.g., the interpupillary distance PD) of the wearer.

The methods and device for measuring the pupil distance according to the embodiments are capable of obtaining the accurate pupil distance steadily, easily and at a low cost. It is understood that the methods and device for measuring the pupil distance according to the embodiments are useful in a manufacturing process of the binocular magnifying glasses for surgery.

There are two types of the binocular magnifying glasses. One of the two types of the binocular magnifying glasses is configured such that an interval between two magnifying optical systems is adjustable (hereafter, referred to as an interval adjustable type). The other of the two types of the binocular magnifying glasses is configured such that the interval between the magnifying optical systems is fixed (hereafter, referred to as a fixed-interval type). The fixed-interval type has an advantage that the interval between the magnifying optical systems hardly changes with time in comparison with the interval adjustable type.

Accordingly, the methods and device for measuring the pupil distance according to the embodiments are useful particularly in a manufacturing process of the fixed-interval type of the binocular magnifying glasses for surgery.

Although the present invention has been described in considerable detail with reference to certain preferred embodiments thereof, other embodiments are possible.

For example, one of various types of imaging devices including a digital camera and a video camera can be used as the camera 30.

The present disclosure relates to the subject matter contained in Japanese Patent Application No. 2003-341642, filed on Sep. 30, 2003, which is expressly incorporated herein by reference in its entirety.

What is claimed is:

1. A method of measuring a pupil distance, comprising:
locating an imaging device at a position a predetermined distance away from a member attached to eyeglasses worn by a subject, the member having two indicators;
photographing the subject while the subject observes an observing point in the vicinity of the imaging device;
measuring an apparent distance between left and right pupils of the subject on a photographed image; and
obtaining an interpupillary distance PD in accordance with:

$$PD = [(A+B) \times C \times E]/(A \times D) \qquad (1)$$

where "A" represents a distance between the member and the imaging device, "B" represents a distance between a center of rotation of each eye of the subject and the member, "C" represents an actual distance between the indicators in a direction parallel with a line connecting left and right centers of rotation of the subject, "D" represents an apparent distance between the indicators in the direction parallel with the line connecting the left and right centers of rotation on the photographed image, and "E" represents the apparent distance between the left and right pupils of the subject on the photographed image.

2. The method according to claim 1, wherein the imaging device is located at the position such that an optical axis of an imaging optical system of the imaging device is substantially included in a reference plane which is orthogonal to the line connecting the left and right centers of rotation of eyes of the subject and includes a center line of a bridge of a nose of the subject.

3. The method according to claim 1, wherein the member is formed to be a plate member.

4. A method of measuring a pupil distance, comprising:
locating an imaging device at a position a predetermined distance away from a member attached to eyeglasses worn by a subject, the member having two indicators;
photographing the subject while the subject observes an observing point in the vicinity of the imaging device;
measuring apparent distances between a center line of a bridge of a nose of the subject and centers of left and right pupils of the subject on a photographed image; and
obtaining a left monocular pupil distance PDL and a right monocular pupil distance PDR in accordance with:

$$PDL=[(A+B)\times C\times EL]/(A\times D) \quad (2)$$

$$PDR=[(A+B)\times C\times ER]/(A\times D) \quad (3)$$

where "A" represents a distance between the member and the imaging device, "B" represents a distance between a center of rotation of each eye of the subject and the member, "C" represents an actual distance between the indicators in a direction parallel with a line connecting left and right centers of rotation of the subject, "D" represents an apparent distance between the indicators in the direction parallel with the line connecting the left and right centers of rotation on the photographed image, "EL" represents an apparent distance between the center line of the bridge of the nose of the subject and the center of the left pupil of the subject on the photographed image, and "ER" represents an apparent distance between the center line of the bridge of the nose of the subject and the center of the right pupil of the subject on the photographed image.

5. The method according to claim 4, wherein the imaging device is located at the position such that an optical axis of an imaging optical system of the imaging device is substantially included in a reference plane which is orthogonal to the line connecting the left and right centers of rotation of eyes of the subject and includes the center line of the bridge of the nose of the subject.

6. The method according to claim 4, wherein the member is formed to be a plate member.

7. A method of measuring a pupil distance, comprising:
locating an imaging device at a position a predetermined distance away from a member attached to eyeglasses worn by a subject, the member having two indicators;
photographing the subject while the subject observes an observing point in the vicinity of the imaging device;
measuring apparent distances between a center line of a bridge of a nose of the subject and centers of left and right pupils of the subject on a photographed image;
obtaining an angle θ formed between an optical axis of an imaging optical system of the imaging device and a reference plane which is orthogonal to a line connecting left and right centers of rotation of eyes of the subject and includes the center line of the bridge of the nose of the subject; and
obtaining a left monocular pupil distance PDL and a right monocular pupil distance PDR in accordance with:

$$PDL=[(A+B)\times EL\times C/(D\times A)]B\times \tan\theta \quad (4)$$

$$PDR=[(A+B)\times ER\times C/D+A\times B\times \tan\theta]/(A+2B) \quad (5)$$

where "A" represents a distance between the member and the imaging device, "B" represents a distance between the center of rotation of each eye of the subject and the member, "C" represents an actual distance between the indicators in a direction parallel with the line connecting the left and right centers of rotation of the subject, "D" represents an apparent distance between the indicators in the direction parallel with the line connecting the left and right centers of rotation on the photographed image, "EL" represents an apparent distance between the center line of the bridge of the nose of the subject and the center of the left pupil of the subject on the photographed image, and "ER" represents an apparent distance between the center line of the bridge of the nose of the subject and the center of the right pupil of the subject on the photographed image.

8. The method according to claim 7,
wherein the eyeglasses has a projection protruding toward a front side of the eyeglasses, and
wherein the angle θ is obtained based on an image of the projection on the photographed image.

9. The method according to claim 7, wherein the member is formed to be a plate member.

10. A method of measuring a pupil distance, comprising:
locating an imaging device at a position a predetermined distance away from a member attached to eyeglasses worn by a subject, the member having distance scale marks;
photographing the subject while the subject observes an observing point in the vicinity of the imaging device;
measuring a distance between left and right pupils of the subject on a photographed image using the distance scale marks of the member on the photographed image; and
obtaining an interpupillary distance PD in accordance with:

$$PD=[(A+B)\times F]/A \quad (6)$$

where "A" represents a distance between the member and the imaging device, "B" represents a distance between a center of rotation of each eye of the subject and the member, and "F" represents a distance between visual axes at a position of the member.

11. The method according to claim 10, wherein the imaging device is located at the position such that an optical axis of an imaging optical system of the imaging device is substantially included in a reference plane which is orthogonal to a line connecting left and right centers of rotation of eyes of the subject and includes a center line of a bridge of a nose of the subject.

12. A method of measuring a pupil distance, comprising:
locating an imaging device at a position a predetermined distance away from a member attached to eyeglasses worn by a subject, the member having distance scale marks;
photographing the subject while the subject observes an observing point in the vicinity of the imaging device;

measuring distances between a center line of a bridge of a nose of the subject and centers of left and right pupils of the subject on a photographed image using the distance scale marks of the member on the photographed image; and obtaining a left monocular pupil distance PDL and a right monocular pupil distance PDR in accordance with:

$$PDL=[(A+B)\times FL]/A \quad (7)$$

$$PDR=[(A+B)\times FR]/A \quad (8)$$

where "A" represents a distance between the member and the imaging device, "B" represents a distance between a center of rotation of each eye of the subject and the member, "FL" represents the distance between the center line of the bridge of the nose of the subject and the center of the left pupil of the subject measured on the photographed image using the distance scale marks of the member on the photographed image, and "FR" represents the distance between the center line of the bridge of the nose of the subject and the center of the right pupil of the subject measured on the photographed image using the distance scale marks of the member on the photographed image.

13. The method according to claim 12, wherein the imaging device is located at the position such that an optical axis of an imaging optical system of the imaging device is substantially included in a reference plane which is orthogonal to a line connecting left and right centers of rotation of eyes of the subject and includes the center line of the bridge of the nose of the subject.

14. A method of measuring a pupil distance, comprising:

locating an imaging device at a position a predetermined distance away from a member attached to eyeglasses worn by a subject, the member having distance scale marks;

photographing the subject while the subject observes an observing point in the vicinity of the imaging device;

measuring distances between a center line of a bridge of a nose of the subject and centers of left and right pupils of the subject on a photographed image using the distance scale marks of the member on the photographed image;

obtaining an angle θ formed between an optical axis of an imaging optical system of the imaging device and a reference plane which is orthogonal to a line connecting left and right centers of rotation of eyes of the subject and includes the center line of the bridge of the nose of the subject; and obtaining a left monocular pupil distance PDL and a right monocular pupil distance PDR in accordance with:

$$PDL=[(A+B)\times FL/A]+B\times \tan\theta \quad (9)$$

$$PDR=[(A+B)\times FR+A\times B\times \tan\theta]/(A+2B) \quad (10)$$

where "A" represents a distance between the member and the imaging device, "B" represents a distance between a center of rotation of each eye of the subject and the member, "FL" represents the distance between the center line of the bridge of the nose of the subject and the center of the left pupil of the subject measured on the photographed image using the distance scale marks of the member on the photographed image, and "FR" represents the distance between the center line of the bridge of the nose of the subject and the center of the right pupil of the subject measured on the photographed image using the distance scale marks of the member on the photographed image.

15. The method according to claim 14, wherein the eyeglasses has a projection protruding toward a front side of the eyeglasses, and wherein the angle θ is obtained based on an image of the projection on the photographed image.

* * * * *